(12) United States Patent
Chamchoum

(10) Patent No.: US 12,290,159 B2
(45) Date of Patent: *May 6, 2025

(54) FROZEN SKIN SERUM AND APPLICATOR THEREOF

(71) Applicant: Christina Chamchoum, Los Angeles, CA (US)

(72) Inventor: Christina Chamchoum, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/614,696

(22) Filed: Mar. 24, 2024

(65) Prior Publication Data

US 2024/0225239 A1 Jul. 11, 2024

Related U.S. Application Data

(63) Continuation of application No. 17/306,794, filed on May 3, 2021, now Pat. No. 11,937,683.

(51) Int. Cl.
*A45D 40/26* (2006.01)
*A61K 8/02* (2006.01)
*A61K 8/34* (2006.01)
*A61K 8/67* (2006.01)
*A61K 8/73* (2006.01)
*A61K 8/9789* (2017.01)
*A61K 8/9794* (2017.01)
*A61Q 19/00* (2006.01)

(52) U.S. Cl.
CPC .......... *A45D 40/261* (2013.01); *A61K 8/0216* (2013.01); *A61K 8/342* (2013.01); *A61K 8/676* (2013.01); *A61K 8/735* (2013.01); *A61K 8/9789* (2017.08); *A61K 8/9794* (2017.08); *A61Q 19/00* (2013.01); *A61K 2800/874* (2013.01)

(58) Field of Classification Search
CPC .... A45D 40/261; A45D 34/041; A61K 8/735; A61K 8/676; A61K 8/9798; A61K 8/9794; A61K 8/342; A61K 2800/874; A61Q 19/00
USPC ......................................... 401/209, 215, 219
See application file for complete search history.

(56) References Cited

U.S. PATENT DOCUMENTS 10,682,280 B2 * 6/2020 Loughrey .............. A61H 15/00

* cited by examiner

*Primary Examiner* — David J Walczak

(57) ABSTRACT

A frozen serum and applicator thereof may include a mold having a first half releasably engaged with a second half. When engaged, the first half and the second half may form a reservoir therebetween to accept a volume of a serum. The serum may be frozen within the mold to produce a frozen serum having at least one receiver molded thereon to releasable engage with an applicator configured to permit the frozen serum to be rolled. An opening may be provided on the mold to permit the serum to be disposed within the reservoir.

20 Claims, 3 Drawing Sheets

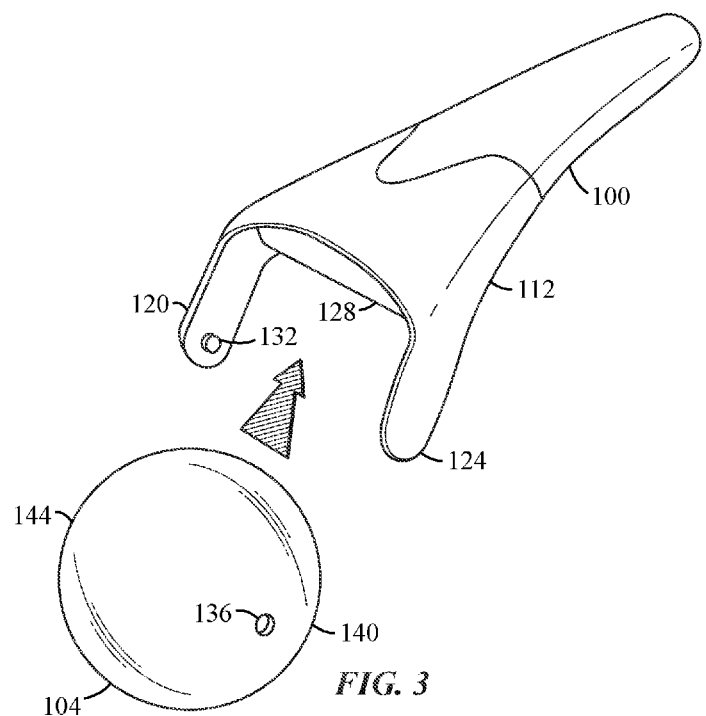
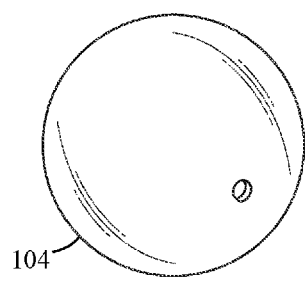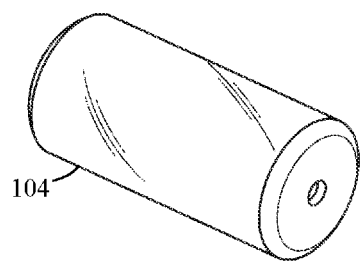
FIG. 3
FIG. 4     FIG. 5

FROZEN SKIN SERUM AND APPLICATOR THEREOF

This application is a continuation application of and claims the benefit of U.S. patent application Ser. No. 17/306,794, filed on May 3, 2021, the contents of which are hereby incorporated in their entirety.

TECHNICAL FIELD

Embodiments of the invention relate to skincare products and more particularly relate to frozen skin serums and applicators thereof.

BACKGROUND

Cosmetic packaging often includes an applicator that is suitable for dispensing the particular cosmetic. Skincare products may include a cream, serum, or other liquid, gel, emulsion, etc. which is spread onto the skin using the applicator. In some instances, the applicator may function to massage the skin at the application site. It is believed that cooling the skin may have various benefits, such as by reducing inflammation associated with puffiness. For example, many believe that cooling the skin below the eyes will reduce eye puffiness.

In the current arts, rollers are pre-chilled to cool the roller surface which can be applied to the skin. Similarly, some will cool cosmetics prior to applying the cosmetic. However, this results in a limited cooling effect as the cosmetic quickly raises temperature upon contact with the skin.

SUMMARY

This summary is provided to introduce a variety of concepts in a simplified form that is disclosed further in the detailed description of the embodiments. This summary is not intended to identify key or essential inventive concepts of the claimed subject matter, nor is it intended for determining the scope of the claimed subject matter.

The embodiments provided herein relate to a frozen serum and applicator thereof, including a mold having a first half releasably engaged with a second half. When engaged, the first half and the second half form a reservoir therebetween to accept a volume of a serum. The serum is frozen within the mold to produce a frozen serum having at least one receiver molded thereon to releasable engage with an applicator configured to permit the frozen serum to be rolled. An opening is provided on the mold to permit the serum to be disposed within the reservoir.

The skin serum is disposed within a mold and frozen prior to use. The mold is designed to retain the serum within the mold while freezing while shaping the serum into a configuration compatible with the applicator such that the frozen serum may be removed from the mold and releasably engaged with the applicator.

In one aspect, the serum is comprised of at least one of the following: hyaluronic acid, vitamin C, jojoba oil, aloe vera, and retino.

In one aspect, the serum has a freezing temperature of about 0° Celsius.

In one aspect, the applicator includes a handle portion positioned at a first end of the applicator.

In one aspect, the applicator includes a receiver portion positioned at the second end of the applicator.

In one aspect, the receiver portion includes a first arm and a second arm.

In one aspect, the first arm and the second arm each include a protrusion to interface with the at least one receiver on the frozen serum to permit the frozen serum to be rolled.

In one aspect, the first arm and the second arm are flexible.

In one aspect, the frozen serum is shaped as a sphere or as a cylinder.

In one aspect, the handle portion releasably engages with the receiver portion.

In one aspect, the frozen serum is melted and reused in future applications.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein:

FIG. 3 illustrates an exploded view of the applicator having the frozen serum removed from the applicator, according to some embodiments;

FIG. 4 illustrates a perspective view of the frozen serum shaped as a sphere, according to some embodiments;

FIG. 5 illustrates a perspective view of the frozen serum shaped as a cylinder, according to some embodiments.

DETAILED DESCRIPTION

Figure 1:
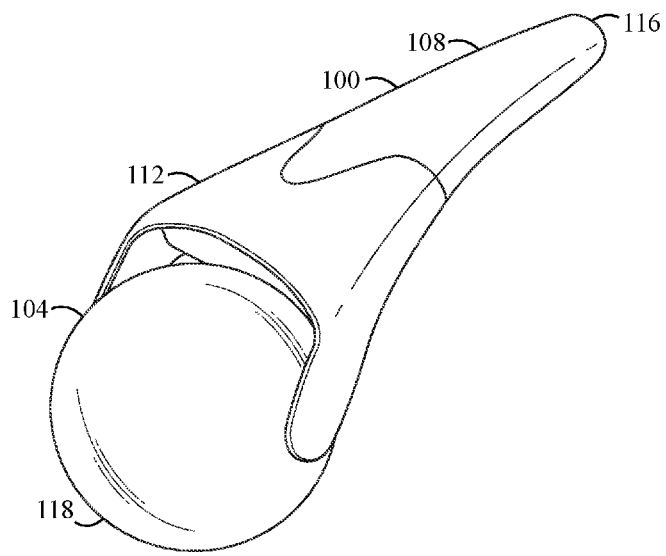
FIG. 1 illustrates a perspective view of the applicator and frozen serum, according to some embodiments.

The above and other elements, features, steps, and concepts of the present disclosure will be more apparent from the following detailed description in accordance with example embodiments of the invention, which will be explained with reference to the accompanying drawings.

It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations, and elements illustrated in the drawings are not necessarily shown to scale. Rather, the various elements are represented such that their function and general purpose become apparent to a person skilled in the art. Any connection, or communication, or coupling between functional blocks, devices, components, or other physical or functional units shown in the drawings or described herein may also be implemented by an indirect connection or coupling.

Various example embodiments will be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, etc.

Specific structural and functional details disclosed herein are merely representative for purposes of describing example embodiments of the present invention. This invention may, however, be embodied in many alternate forms and should not be construed as limited to only the embodiments set forth herein.

Use of a quantitative term or value is not limited to the exact amount recited. For example, presence of the term "about" indicates an intention to convey that the same result can be achieved by using a value that is not exactly that recited. Similarly, if an objective can be achieved by using less than all of a specified amount, it may be so indicated through use of the term "substantial" or "substantially." For example, fifty percent of a value may be considered substantial when the same result can be achieved as if 100% of a value is used. If an exact amount is required in order to achieve a result, it will be specifically stated.

The specific details of the single embodiment or variety of embodiments described herein are set forth in this application. Any specific details of the embodiments are used for demonstration purposes only, and no unnecessary limitation or inferences are to be understood therefrom.

Before describing in detail exemplary embodiments, it is noted that the embodiments reside primarily in combinations of components related to the system. Accordingly, the device components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

In general, the embodiments described herein relate to a frozen skin serum and applicator thereof. The skin serum is disposed within a mold and frozen prior to use. The mold is designed to retain the serum within the mold while freezing while shaping the serum into a configuration compatible with the applicator such that the frozen serum may be removed from the mold and releasably engaged with the applicator.

Figure 2:
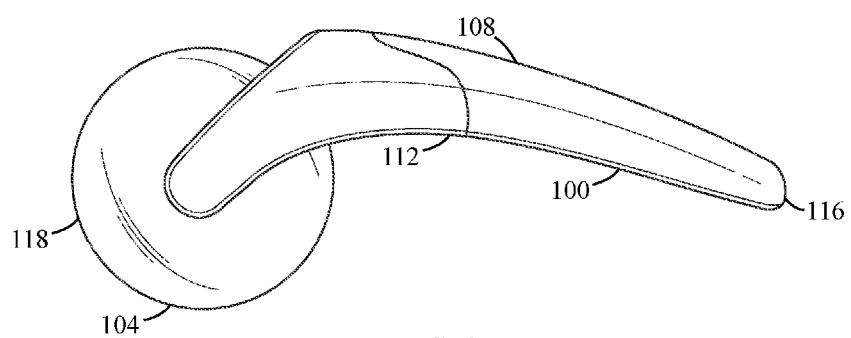
FIG. 2 illustrates a side elevation view of the applicator and frozen serum, according to some embodiments.

FIG. 1 and FIG. 2 illustrate the applicator 100 and frozen serum 104. The applicator 100 includes a handle portion 108 to permit the user to hold the applicator 100 while applying the frozen serum 104 onto their skin. The handle portion 108 extends to a receiver portion 112 configured to releasable engage with the frozen serum 104. The handle portion 108 is positioned at a first end 116 of the applicator 100 and the frozen serum 104 is positioned at the second end 118 of the application 100. The handle portion 108 may be ergonomically shaped to provide a comfortable interface between the handle and the user's hand. Further, the handle portion 108 allows the user to apply pressure when rolling and applying the frozen serum 104 onto the skin.

In some embodiments, the handle portion 108 is integrally molded to the receiver portion 112. Alternatively, the handle portion 108 may be releasable engaged with the receiver portion 112 to permit the user to interchange receiving portion which accommodate various sizes, shapes, and configurations of frozen serums 104.

FIG. 3 illustrates an exploded view of the applicator 100 having the frozen serum 104 removed from the receiver portion 112. The receiver portion 112 include a first arm 120 and a second arm 124 separated by a central portion 128. The frozen serum 104 is dimensioned such that the first arm 120 and second arm 124 at least partially contact the edge of the frozen serum 104 and allow the frozen serum 104 to rotate when being applied to the skin. Each arm 120, 124 includes a protrusion 132 to releasably engage with a receiver 136 on each side 140,144 of the frozen serum 104. In such, the frozen serum 104 is retained on the applicator 100 throughout use and during storage when not in use.

In some embodiments, the first and second arms 120, 124 are constructed of a flexible material such that the first and second arms 120, 124 can bend to accommodate frozen serums 104 of various sizes, shapes, and configuration. This may be especially useful as the frozen serum 104 melts during use.

FIG. 4 and FIG. 5 illustrate the frozen serum 104 in a spherical (see FIG. 4) and cylindrical (see FIG. 4) configuration. One skilled in the arts will readily understand that the size, shape, and configuration may be changed based on user preference, or particular applicator shape and size. Further, while shapes which can roll (e.g., spheres, cylinders, ovoids, etc.) may be most convenient for the user to promote even melting of the frozen serum 104, the shape may be other shapes including cubes. The frozen serum 104 may be formulated from various skincare ingredients known in the arts, and especially from compositions which freeze at 0° Celsius. For example, the frozen serum can include hyaluronic acid, vitamin C, jojoba oil, aloe vera, retino, and combinations thereof. The composition may include various surfactants, thickening agents, solids (including soluble and insoluble solids), fragrances, colorants, and the like which may provide the desired effect, treatment, aesthetic appearance, and scent to the frozen serum composition.

Figure 6:
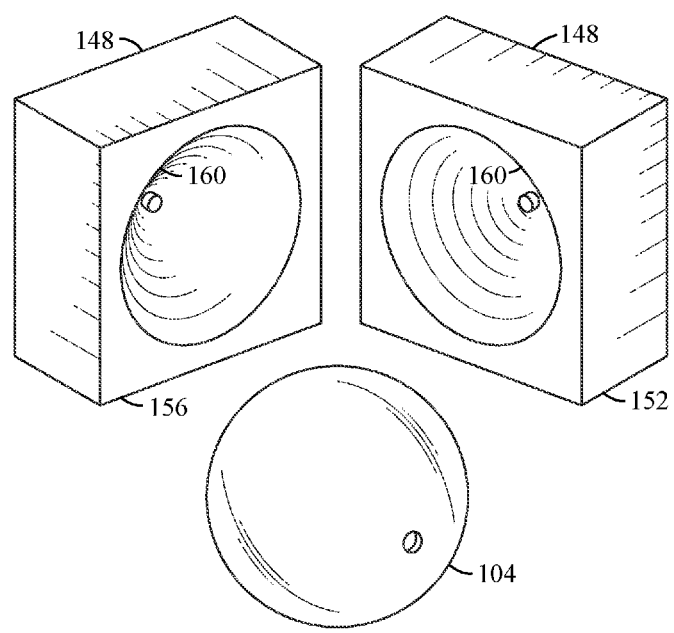
FIG. 6 illustrates a perspective view of the mold and frozen serum, according to some embodiments.

FIG. 6 illustrates a perspective view of the mold 148 and frozen serum 104 separated therefrom. The mold 148 includes an opening to permit the mold to be at least partially filled with the serum composition prior to freezing the serum composition. The opening may include a cap to allow the user to dispense the serum therein prior to freezing. The cap may also relieve pressure within the reservoir if overfilled with serum. The mold 148 may include a half 152 separable from a second half 156 to allow the mold to open and the frozen serum 104 to be removed from the mold 148. During use, the first half 152 and second half 156 are placed together to form a reservoir 160 wherein the serum composition is disposed and the frozen serum is formed. The reservoir 160 is able to be filled with and retain a skin care product that is a liquid or semi-liquid at standard atmospheric pressure and temperature, and that freezes at lower temperatures. Many types of personal care products will freeze at temperatures substantially close to 0° C., but those that freeze at higher or lower temperatures may also be useful. The reservoir 160 should be able to withstand serum expansion and contraction without rupturing. It should also be non-reactive with the products that it is intended to hold. In such, reservoir may be fashioned out of elastic materials, such as thermoplastic elastomers or silicone rubbers.

In some embodiments, the frozen serum 104 may be used without the applicator 100. In such instances, the user simply holds the frozen serum 104 in their hand and applies the frozen serum onto their skin.

In some embodiments, once the frozen serum 104 has been applied to the skin, the frozen serum may be melted and redisposed with additional serum into the mold.

In some embodiments, the mold may be pre-filled at the time of manufacture, and/or may be refilled by the user. When the mold is filled at the factory, the reservoir will be filled by any means known in the field of personal care products, such as being dispensed under pressure through a filling nozzle. Whether the mold is sold filled or empty, a supply of serum will be separately provided so that the consumer can fill the mold as needed. The separately supplied product is a liquid and can be dispensed into the mold from a container in which the serum is provided. Typically, the serum to be filled will be in a liquid state, at a temperature above the freezing point of the product.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

It will be appreciated by persons skilled in the art that the present embodiment is not limited to what has been particularly shown and described hereinabove. A variety of modifications and variations are possible in light of the above teachings without departing from the following claims.

What is claimed is:

1. An applicator and mold for a frozen serum, comprising:
the mold having a first half releasably engagable with a second half, the first half and the second half configured to form a reservoir therebetween to accept a volume of the serum,
wherein the mold is configured to produce a shaped frozen serum; and the mold including a pin configured to define at least one receiver in the produced shaped frozen serum, the receiver configured to releasably engage with the applicator;
wherein the applicator includes a handle portion positioned at a first end of the applicator, and a receiver portion positioned at a second end of the applicator and comprising a first arm and a second arm, and
wherein the first arm and the second arm comprise a protrusion to interface with the at least one receiver on the produced shaped frozen serum.

2. The applicator and mold for a frozen serum applicator of claim 1, wherein the first arm is a flexible arm.

3. The applicator and mold for a frozen serum applicator of claim 2, wherein the second arm is a flexible arm.

4. The applicator and mold for a frozen serum applicator as recited in claim 1, wherein the protrusion defines an axis of rotation of a produced frozen serum about the protrusion.

5. The applicator and mold for a frozen serum applicator of claim 1, wherein the first half and second half are configured to form a reservoir that is a sphere.

6. A mold for a frozen serum, comprising:
the mold having a first half; and
a second half, the first half releasably engagable with the second half, the first half and the second half configured to form a reservoir therebetween to accept a volume of the serum, wherein the mold is configured to produce a shaped frozen serum defining at least one receiver molded thereon, the applicator configured to releasably and rotatably engage with the produced frozen serum; and
an opening defined in the mold that is configured to permit the serum to be disposed within the reservoir.

7. The mold of claim 6, wherein the applicator includes a handle portion positioned at a first end of the applicator.

8. The mold of claim 7, wherein the applicator includes a receiver portion positioned at a second end of the applicator.

9. The mold of claim 8, wherein the receiver portion includes a first arm and a second arm.

10. The mold of claim 9, wherein the first arm and the second arm each include a protrusion to interface with the at least one receiver on the produced frozen serum to permit the produced frozen serum to be rolled.

11. The mold of claim 10, wherein the first half and second half are configured to form a reservoir that is a sphere.

12. The mold of claim 10, wherein the first half and second half are configured to form a reservoir that is a cylinder.

13. The mold of claim 12, wherein the handle portion releasably engages with the receiver portion.

14. The mold of claim 13, wherein the mold is configured to shape a frozen serum that is meltable and reusable.

15. An applicator and mold for a frozen serum, comprising:
the mold having a first half; and
a second half, the first half releasably engagable with the second half, the first half and the second half configured to form a reservoir therebetween to accept a volume of the serum, wherein the mold is configured to produce a shaped frozen serum defining at least one receiver molded thereon, the applicator configured to releasably and rotatably engage with the produced frozen serum;
an opening defined in the mold that is configured to permit the serum to be disposed within the reservoir and frozen therein; and the applicator including a handle portion and a receiver portion, the receiver portion including a first arm and a second arm to retain the produced frozen serum thereon.

16. The applicator and mold for a frozen serum of claim 15, wherein the handle portion is positioned at a first end of the applicator and the receiver portion is positioned at a second end of the applicator, the first end opposing the second end.

17. The applicator and mold for a frozen serum of claim 16, wherein the receiver portion includes a first arm and a second arm, each including a protrusion configured to interface with the at least one defined receiver and further configured to be an axis of rotation of the produced frozen serum about the protrusions.

18. The applicator and mold for a frozen serum of claim 15, wherein the first half and second half are configured to form a reservoir that is a sphere.

19. The applicator and mold for a frozen serum of claim 15, wherein the first half and second half are configured to form a reservoir that is a cylinder.

20. The applicator and mold for a frozen serum of claim 15, wherein the handle portion releasably engages with the receiver portion.

* * * * *